United States Patent [19]
Apel

[11] 4,192,254
[45] Mar. 11, 1980

[54] FLOATABLE BEDDING

[76] Inventor: Richard L. Apel, 1924 Myrtlewood Dr., Ceres, Calif. 95307

[21] Appl. No.: 902,176

[22] Filed: May 2, 1978

Related U.S. Application Data

[63] Continuation of Ser. No. 758,931, Jan. 13, 1977, abandoned.

[51] Int. Cl.$^2$ ............................................. A01K 67/00
[52] U.S. Cl. ........................................... 119/1; 119/15
[58] Field of Search ................................. 119/1, 2, 15

[56] References Cited

U.S. PATENT DOCUMENTS

| 3,654,903 | 4/1972 | Montgomery | 119/15 |
| 3,698,358 | 10/1972 | Wada et al. | 119/2 |

OTHER PUBLICATIONS

Ian G. Walls, "The Complete Book of Greenhouse Gardening," 1973 pp. 169–171.

*Primary Examiner*—Hugh R. Chamblee
*Attorney, Agent, or Firm*—Jack L. Bohan

[57] ABSTRACT

An improved bedding material for worm growing consisting of a particulate material having a density of less than that of water so as to greatly facilitate the harvesting process after the worms have matured.

5 Claims, 3 Drawing Figures

FLOATABLE BEDDING

This application is a continuation of application Ser. No. 758,931 of Jan. 13, 1977 now abandoned.

BACKGROUND OF THE INVENTION

The industry of growing worms, grubs and the like, for fishing bait and other purposes, has substantially expanded over the years. Although a great deal of advances have been made in the art as far as improved nutrition, breeding, temperature control and other matters affecting growth, there has been little improvement in the time consuming and tedious harvesting process. For example, worms are normally harvested by hand and either counted out or weighed and placed into cartons once they have reached the adult stage.

The present invention provides for a complete departure from the previous tedious practices involved in harvesting. It is well known that worms, and the like, are able to withstand considerable period of submersion in water without any serious impairment to their condition. Moreover, these species of animal life are more dense than water and will rapidly sink to the bottom of any water-holding vessel. Normally, worms are grown in a bed comprised of dirt, straw, and numerous other materials in order to provide them with a matrix for obtaining necessary water and nutrients, as well as providing for a habitat and a place for propagation. However, it has been found that dirt is not an absolute necessity for the propagation of the worms, and the like, and that they can quite satisfactorily live out their life cycle in a matrix devoid of dirt just so long as they are provided with sufficient food, water, warmth, and, when necessary, protection from the elements.

Accordingly, the present invention relies upon the use of a particulate or granulated material which is lighter than water. This bedding material can be used as any other bedding material during the growth stage of the worm, and can be sprinkled or infused with appropriate nutrients and water just as any other bedding material in order to maximize growth. Once the worms have reached the appropriate stage of maturation, they may be harvested by the simple practice of simply adding water to the bedding material causing the buoyant granulated material to float to the surface and the worms, extra feed, castings, and other debris to move to the bottom. By use of appropriate screening of various sizes, the worms and egg capsules may be separated from the remaining debris and harvested.

It has heretofore been difficult to obtain a clean harvest of egg capsules from the bedding, frequently requiring that old bedding be re-used. However, by use of the present technique, egg capsules can be harvested separately with an extremely high degree of recovery and the floatable bedding can be completely washed and, if necessary, sterilized prior to re-introduction of the eggs into the bedding material for a new cycle of growth.

BRIEF DESCRIPTION OF THE DRAWINGS

FIG. 1 B is a vertical cross-sectional view of a tank and screen apparatus for separating components of the habitat during harvest.

DETAILED DESCRIPTION

Figure 1A:
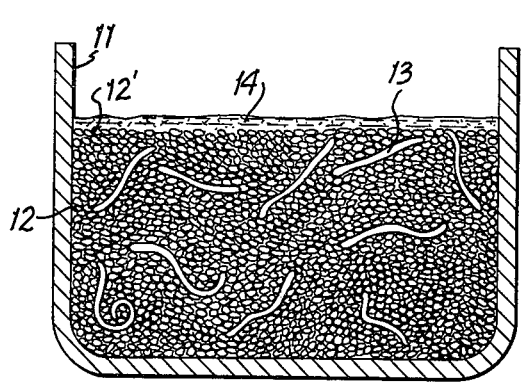
FIG. 1 A is a vertical cross-sectional view of a tank containing the habitat bedding of the present invention.
Figure 1B:
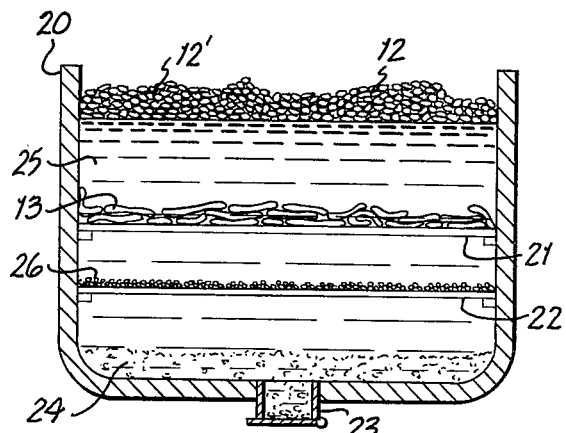

Referring now to FIGS. 1 A and 1 B reference numeral 11, designates a tank containing bedding material 12 comprised of the floatable particulate or granulated material of the present invention. Contained within this particulate material are numerous worms 13, or the like, which are being propagated in bed 12. The nutritional needs of the worms are provided by means of adding feed and water at layer 14 at the top of bedding material 12. Any appropriate feed material may be used, as is well known in the worm breeding art. The bedding material 12 is comprised of individual particulate or granular units 12' which are sufficiently small to discourage the worm from attempting to enter into the particle 12' and develop a habitat within the particle. An ideal material has been found to be polystyrene which has been ground into relatively small particles, or polystyrene beads. This particular material has been found to have a surface texture which encourages the worms to burrow between the interstices thereof, and moreover, is sufficiently smooth to discourage the worms from clinging to the particles once the separation process is underway during harvest. It is, of course, within the skill of the art to provide improvements such as injecting the feed and water into the bedding 12 by appropriate means, or by gentle agitation of the bedding in order to stimulate the movement of the worms and a movement of moisture and food throughout the entire depth of the bedding.

To the right of tank 11 is tank 20 which contains a screen 21 of comparatively coarse grid, and screen 22 of a finer grid. At the bottom of tank 20 there is provided a drain 23 for the removal of any debris 24 which settles to the bottom of the tank. Once the worms have completed their growth cycle in tank 11, the tank 11 may then be inverted over tank 20 to cause the bedding to fall on top of screen 21. At the same time a large amount of water is added to the tank 20 causing the bedding 12 to rise to the surface and the worms, egg capsules, excees feeding material, castings, and other foreign material to sink downwardly through the water. The screen 21 catches the worms and allows the other materials to pass therethrough. The screen 22 catches the egg capsules 26 but allows the feed material and other debris to pass therethrough. The bedding material can be agitated while the water is being added so as to further facilitate the separation of the worms from the other materials. The bedding 12 is then floated to the top and skimmed off into an appropriate container leaving the screen 21 containing the worms on top thereof in full view. Screen 21 is then removed from the water 25 and taken to an appropriate area for placement of worms into appropriate shipping containers. Screen 22 can then be removed to retrieve the egg capsules which may be placed in an appropriate area for storage pending the washing of the bedding material so as to begin a new cycle of worm propagation. By this time the other debris and worm castings have settled to the bottom of the tank and the water can be poured off, siphoned, or otherwise disposed of, leaving the castings and debris at the bottom. This material is usually highly sought after by horticulturists for plant propagation and gardening. It, too, can therefore be retrieved and placed into appropriate storage containers pending packaging and sale for those purposes.

Once the bedding 12 has been appropriately rewashed, and, if necessary, sterilized, it may then be placed back into tank 11 with the egg capsules being distributed therein. Then water and appropriate food nutrients are placed on the surface of bedding 12. If necessary, heating pads can also be added in order to assure hatching even in cold weather.

Figure 2:
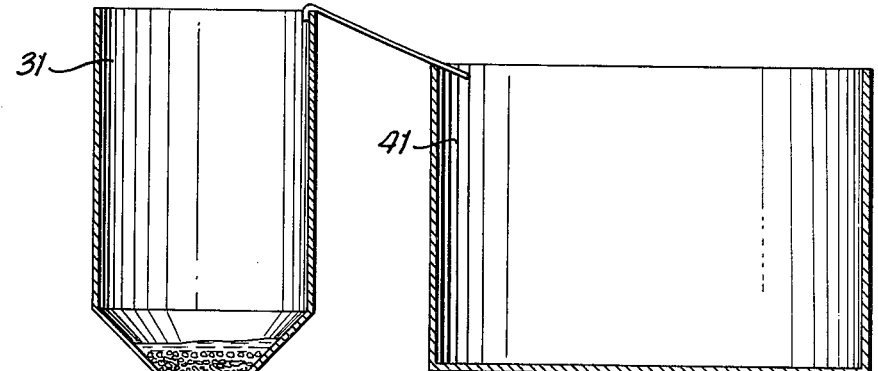
FIG. 2 is an elevation view of larger scale processing system of the present invention, shown in cross-section.
Figure 2:
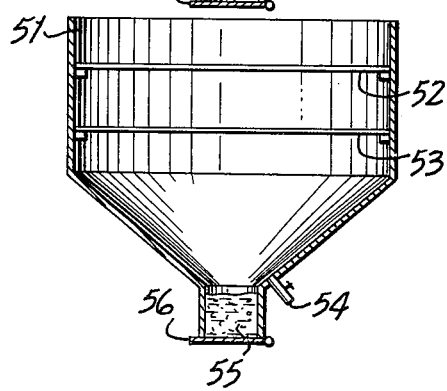

Referring now to FIG. 2, a permanent harvesting facility can be set up for large capacity handling of the worm bedding of the present invention. The bedding containing the worms ready for harvest can be dumped into tank 31 and water is added so as to cause the bedding to float to the surface of tank 31 and cross over into tank 41. Once substantially all the bedding has been retrieved from tank 31 and is placed in tank 41, the valve 32 at the bottom of 31 may be opened so as to allow the precipitant of worms, egg capsules, castings, and other materials, to flow into tank No. 51 which contains filters 52 and 53 with appropriate gridwork so as to catch the worms and egg capsules, respectively. Once the filters 52 and 53 have been removed so as to permit the harvesting of the worms and eggs, respectively, the water can be drained off by means of opening valve 54. The precipitant 55 located in the bottom of tank 51 may then be removed by opening the large valve No. 56. This material which is rich in worm castings can then be packaged for appropriate marketing.

Although polystyrene in a granulated or bead form has been found to be a highly desirable material for use as bedding 12, it is to be understood that any particulate material which has a density less than that of water can be used without departing from the spirit of the present invention. Moreover, it is understood that this bedding material may be used for any type of breeding and cultivation of animal life, such as, grubs and possibly certain types of small sea animals, such as, shrimp.

In the description above, water has been referred to as the fluid medium suitable for the separation of the bedding from the organism, however, any fluid that is non-injurious to the organism may be used. For example, forced air rising in a hollow shaft or column could be used to blow the lightweight bedding upwardly while the organism moves downwardly in the column.

Although there has been shown and described above the particular embodiments of this invention, it will be obvious to those skilled in the art that various changes and modifications may be made therein without departing from the invention. Accordingly, certain modifications and alterations will occur to those skilled in the art that are included within the scope of the following claims.

I claim:

1. A life-cycle habitat for cultivating animal life such as worms and the like comprising a particulate material having a specific gravity of less than 1.0 and having a size and surface smoothness so as to inhibit the animal life such as worms and the like from burrowing into or clinging to said particulate material, and in admixture therewith, food matter for the support of said animal life whereby the animal life such as worms and the like being cultivated in said habitat can be readily separated from the components of said habitat by transferring the habitat containing said animal life to a container of water which will cause separation of said animal life from said particulate material.

2. A habitat as in claim 1 wherein the particulate material is polystyrene.

3. In a process for the cultivation of animal life such as worms and the like comprising:
   (a) providing a bedding of particulate material which is buoyant with respect to water and is of a size and surface smoothness as to inhibit the animal life such as worms and the like from burrowing into or clinging to said particulate material;
   (b) distributing within said bedding a predetermined quantity of said animal life;
   (c) providing nutrients to said organisms until a predetermined degree of maturation of the animal life has occured; and
   (d) separating said animal life from the bedding by adding water thereto whereby the buoyant particulate material floats to the surface of the water and the animal life sinks.

4. In a process as in claim 3 wherein the animal life consists of earthworms.

5. In a process as in claim 4 wherein the particulate material is polystyrene.

* * * * *